United States Patent [19]

Carlson

[11] Patent Number: 5,043,009
[45] Date of Patent: Aug. 27, 1991

[54] PROCESS FOR TREATING PLANTS

[75] Inventor: Danis R. Carlson, Blaine, Minn.

[73] Assignee: Dan Carlson Scientific Enterprises, Inc., Blaine, Minn.

[21] Appl. No.: 358,391

[22] Filed: May 26, 1989

Related U.S. Application Data

[60] Division of Ser. No. 76,046, Jul. 21, 1987, Pat. No. 4,834,789, which is a continuation-in-part of Ser. No. 802,477, Nov. 27, 1985, Pat. No. 4,680,889, which is a continuation of Ser. No. 792,617, Oct. 22, 1985, abandoned, which is a continuation of Ser. No. 518,008, Jul. 28, 1983, abandoned, which is a continuation of Ser. No. 286,260, Jul. 23, 1981, abandoned.

[51] Int. Cl.$^5$ ............................................. A01N 43/88
[52] U.S. Cl. ........................................... 71/91; 71/88; 71/92; 71/93; 71/86; 71/100; 71/105; 71/109; 71/115; 71/117; 71/120; 71/121; 71/118; 47/58
[58] Field of Search .................... 71/91, 1; 47/58, 1.3, 47/DIG. 12

[56] References Cited

U.S. PATENT DOCUMENTS

| | | | |
|---|---|---|---|
| 3,499,437 | 3/1970 | Balamuth | 47/1.3 |
| 3,550,586 | 12/1970 | Balamuth | 47/58 |
| 4,055,915 | 11/1977 | Charnoe | 47/58 |

OTHER PUBLICATIONS

Thomson, *Agricultural Chemicals, Book II Herbicides,* 1983–84 Revision, pp. 234–235.

*Primary Examiner*—Richard L. Raymond
*Assistant Examiner*—B. Bembenick
*Attorney, Agent, or Firm*—Kinney & Lange

[57] ABSTRACT

The present invention provides a method for controlling weeds, e.g. plant growth, using a combination of a herbicide that is absorbed by the plant, together with the application of sound at a frequency of between 4 and 6 kilohertz at a volume of about 115 decibels to facilitate the uptake of the herbicide by the plant.

9 Claims, No Drawings

PROCESS FOR TREATING PLANTS

This is a Divisional of U.S. patent application Ser. No. 076,046 filed July 21, 1987 issued as U.S. Pat. No. 4,834,789 on May 30, 1989 which is a Continuation-In-Part Application of U.S. patent application Ser. No. 802,477 filed Nov. 27, 1985 now U.S. Pat. No. 4,680,889; which is a continuation of U.S. patent application Ser. No. 792,617 filed Oct. 22, 1985 now abandoned; which is a continuation of U.S. patent application Ser. No. 518,008 filed July 28, 1983 now abandoned; which is a continuation of U.S. patent application Ser. No. 286,260 filed July 23, 1981 now abandoned.

BACKGROUND OF THE INVENTION

The present invention relates to a process for affecting plant growth and, more particularly, includes use of sound waves to assist in the assimilation of growth inhibiting solutions by plants. For example, one may decrease the level of herbicide needed to provide an effective killing dosage, thus minimizing pollution.

SUMMARY OF THE INVENTION

The present invention is a process for treating plants with herbicide and sound of a particular frequency to inhibit growth.

Further, the present invention is a process of treating plants with such sound to force osmosis of growth affecting herbicide compositions into the plants. The process may include the steps of applying the growth affecting composition to the plant and subjecting the plant to sound waves while the composition is disposed on said plant. Alternatively, herbicide compositions may be applied by spraying during the application of sound. A suitable composition may be an aqueous solution of conventional herbicide. Detergent may be included in the solution to facilitate uniform distribution of the aqueous solution on the foliage of the plant.

The sound used in the present invention may be produced using any of a variety of mechanisms. One technique that has proven suitable is the use of a recording, e.g. disc recordings and cassette recordings. Alternatively, electronic sound producing devices may be used.

DETAILED DESCRIPTION OF THE PRESENT INVENTION

The plants are treated with a combination of such sound and herbicide chemicals. Any technique may be used to apply the chemicals to the plants. In the case of applying chemicals as an aqueous solution to the foliage of plants, conventional spraying techniques may be used. In the case of applying the chemicals to seeds, the seeds may be wetted with an aqueous solution.

The plant is subjected to sound waves of high frequency. The sound waves may be produced in any manner, for example, sound recordings or sound generating devices. The sound may be of a frequency of 4 to 6 kilohertz, preferably 4.7 to 5.3 kilohertz. The sound waves may be of a constant frequency; however, use of a variable frequency within this range is preferred. For example, the plants may be subjected to sound waves which vary in frequency from 4.7 to 5.3 kilohertz. The period of one rise and fall in frequency may be from 0.1 to 0.5 seconds. The sound may be pulsating, e.g., discontinuous. Sound waves outside this frequency may also be present.

It is believed the sound waves serve to open the individual plant cells to increase the osmotic movement of chemicals into the plant cells. The volume of the sound waves in the present invention may be at least 115 decibels, preferably 115 to 120 decibels at the point where the sound interfaces with the plant foliage, e.g. plant cells. The duration of sound treatment is at least 15 seconds, preferably about 30 seconds to 30 minutes.

The present process for growth eradication has been found suitable for any undesirable plant growth such as grasses, rag weed, button weed and the like. The present process for plant life inhibition may be carried out using any herbicide together with the sound treatment. For example, any conventional weed spray. The herbicide may be used at a lower level of application and acts more rapidly than conventional use. For example, the herbicide concentration and thus application may be reduced by 5 to 75 percent. Alternatively, the herbicide may be maintained at full strength and have a more potent effect than was the case heretofore.

Depending upon the situation, any particular plant may be considered to be a weed. In a watermelon patch, volunteer tomato plants are weeds. In an apple orchard, maple saplings are weeds. This, the present invention contemplates use of the process on any plant growth that is undesired. Certain plants are well recognized as weeds and as being undesired. Perhaps this is because such plants are common infestations to many cultivated crops. These common weeds are often tenacious and very difficult to eliminate from the crop. Such weeds are often difficult to kill. Use of herbicides has been under attack in recent years for environmental reasons. With the present process, the killing dosage of herbicide is significantly reduced, thus reducing the environmental impact. The present process can also make such herbicide effective on plants where the herbicide has had a marginal effect in the past.

Illustrative of the weeds that may be treated according to the present invention are Canadian thistle, quackgrass, yellow nutsedge, bluegrass, sowthistle, field bindweed, leafy spurge, common milkweed, wirestem muhly, perennial buttercups, germander, bull thistle, cockleburr, chickweed, goldenrod, pigweed, mustards, burdoch, button weed, wild sunflowers, ash, wild blackberry, hawthorne, oak, ivy, sumac, maple, willow, chokeberry, poison ivy, mesquite, brambles, wild grape, honeysuckle, alder, pine, fir, spruce, rag weed, pokeberry, yucca, smartweed, clovers, knotweed, shepherd's purse, crabgrass, foxtail, coffeeweed, teaweed, kochia, velvetleaf, cockles, knapweed, dock, gooseweed, toadtlax, johnsongrass, dandelions, sandburr, groundcherry, morningglory, beggarweed, annual bluegrass, fiddleneck, tarweed, speedwell, shattercane, and the like.

The present process contemplates use of any plant herbicide that functions through the chemical take up by the plant, such herbicide being used together with the application of sound to the plant. The composition may be a member of the group consisting of phenoxy compounds, benzoic acids derivatives, acedic acid derivatives, phthallic acid derivatives, dintro analines, nitrites, admides, acetamides, anilides, carbamates, heterocyclic nitrogen derivatives, urea compounds, metal organics and metal inorganics. The more recognized herbicides include such commercial products as Bladex TM (cyanazine), Eradicane TM (EPTC and dichormid), Lasso-Atrazine TM (alachlor and atrazine), and Roundup TM (glyphosate). The herbicide may be any of a wide variety of compositions having herbicidal properties. Illustrative of commercially available herbicides suitable for the present invention include the following: Amiben TM (e.g. chloramben), Antor TM (e.g. diethatyl), Avenge TM (e.g. atrazine and difenzoquate), Balan TM (e.g. benefin), Banvel TM (e.g. dicamba), Basagran TM (e.g. bentazon), Basalin TM (e.g. fluchloralin), Betamix TM (e.g. desmedipham and phenmedipham), Bicap TM (e.g. atrazine and metochlor), Bladex TM (e.g. cyanazine), Blazer TM (e.g. acifluorfen), Brominal TM (e.g. bromoxynil), Bronate TM (e.g. bromoxynil and MCPA), Bronco TM (e.g. alachlor and glyphosate), Buctril (e.g. bromoxynil), Carbyne 2EC TM (e.g. barban), Classic TM (e.g. DPX-F6025), Command TM (e.g. FMC-57027), Conquest TM (e.g. cyanazine and atrazine), Dowpon M TM (e.g. 2,4-D amine, 2,4-D ester and dalapon), Dual TM (e.g. matàchlor), Eptam TM (e.g. EPTC), Eradicane TM (e.g. EPTC and dichlormid), Far-Go TM (e.g. triallate), Fusilade 2000 TM (e.g. fluazifop-P), Genate Plus TM (e.g. butylate and dichlormid), Gramoxone Super TM (e.g. paraquat), Herbicide 273 TM (e.g. endothall), Hoelon TM (e.g. diclofop), Kerb TM (e.g. pronamide), Laddock TM (e.g. bentazon and atrazine), Lasso TM (e.g. alachor), Lexone (e.g. metribuzin), Lorox TM (e.g. linuron), Marksman TM (e.g. dicamba and atrazine), Modown TM (e.g. MCPA amine, MCPA ester and bifenox), One-Shot TM (e.g. dichiofop, bromoxinil and MCPA), and Tandum TM (e.g. tridiphane). Other suitable herbicides for use in the present invention include Dicamba TM (e.g. 3,6-dichloro-0-anisic acid), Ioxynil TM (e.g. 4-hydroxy 3,5-diiodobenzonitrile), and Pyrazon TM (e.g. 5-amino-4-chloro-2-phenyl-3 (2H)-pyridazinone).

The present invention may be carried out with respect to grasses using such products as CME 127 TM (e.g. 2-chloro-6-nitro-3-phenoxy-aniline), Dyanap TM, Endothall TM (e.g. 7-oxabicyclo (2,2,1) heptane-2,3-dicarboxylic acid), Ethalfluralin TM (e.g. N-ethyl-N-(2-methyl-2-propenyl)-2,6 dinitro-4-(trifluoromethyl) benzenamine), Propanil TM (e.g. 3,4-dichloropropionanilde), CIPC TM (e.g. isopropyl-m-chlorocarbanilate), IPC TM (e.g. ispropoyl-carbanilate), Carbyne TM (e.g. 4-chloro-2-butynyl m-chlorocarbanilate) and Quinclorac TM (e.g. 3,7-dicloro-8-quinoline carboxylic acid).

Where specific herbicides have been suggested here, it is to be recognized that a wide variety of other herbicides may be used in the present invention. For example, the various herbicides listed in the book *Agricultural Chemicals,* Book II, Herbicides, 1986–87, revision by W. T. Thomson, are deemed suitable and incorporated by reference. The various herbicides listed in the Thomson book may be used in amounts well reduced from that suggested by Thomson, for example, at a level of from 95 to 25 percent of those set forth in Thomson. Also, it is to be recognized that the usage of the herbicide may be at full recommended level or even higher to result in herbicide activity well beyond that previously obtained with the particular herbicides.

EXAMPLE I

The present invention was carried out using a post emergent herbicide in combination with the application of sound on grassy weeds. The herbioide was Hoegrass TM produced by Hertz Chemical, Ltd. The active ingredient was diclofop methyl. Twenty liters of concentrate containing 190 grams per liter active ingredient was diluted to 530 gallons by the addition of water. This dilution contained only 25 percent of the usual recommended active ingredient. The diluted solution was applied by a drawn boom-type sprayer at a rate of 10 gallons per acre while sound was applied at a frequency of between 4 and 6 kilohertz and at a transmitted volume of 115 decibels. Although the herbicide, together with sound, was applied at a level of only 25 percent of normal recommended application, the effect on eradicating the grassy weeds, primarily wild oats, was essentially the same as full application using no sound.

EXAMPLE II

The present invention was carried out using a post emergent herbicide (Hoe-grass 2 TM by Hertz Chemical, Ltd.) in combination with sound on broadleaf weeds and grassy weeds. This herbicide included diclofop methyl and bromoxynil having active ingredients of 310 grams per liter. Twenty liters of the herbicide concentrate were diluted with water to 540 gallons which is 25 percent of the usual recommended application concentration. The herbicide was applied at a rate of 10 gallons per acre while applying sound at 4 to 6 kilohertz and at a volume of about 115 decibels for at least 15 minutes. Satisfactory herbicidal results were obtained on a cultivated field having substantial broadleaf and grassy weed infestation.

EXAMPLE III

The present invention was carried out using Saber TM herbicide. Saber is a 1:1 mixture of Bromoxynil and META. The concentrate had 720 grams active ingredient per liter. Twenty gallons of Saber were diluted with water to 540 gallons and applied at the rate of 10 gallons per acre. This application is 25 percent of the recommended dosage. The application was accompanied with sound as described in Example II. The application satisfactorily eradicated the growth of weeds in a cultivated field having a mixture of common weeds.

EXAMPLE IV

The present invention was carried out as described in Example II, however using META Extamene TM. The active ingredient is META amine. The concentrate had 500 grams active ingredient per liter. Similar results were obtained.

EXAMPLE V

The present was carried out using Target TM. The active ingredient was a mixture of decamba, mecoprat and MCTA. The concentrate had 400 grams active ingredient per liter. Dilution and application was as described in Example II. Similar results were obtained.

EXAMPLE VI

The present invention may be carried out using Ortho TM Crab Grass killer. A concentrate having by weight 8 percent octyl ammonium methane arsonate and 8 percent dodecyl ammonium methanearsonate. One tablespoon may be diluted with water to one gallon and applied to 200 square feet of lawn to effectively kill crab grass. Sound is applied at a frequency of between 4 and 6 kilohertz for at least 30 seconds following application of the solution.

EXAMPLE VII

A procedure was carried out to compare the present invention utilizing the combination of sound and herbicide with processing including only treatment with herbicide. A composition was first prepared including 4 pints of Basagran TM herbicide and 150 gallons of water. Five gallons of 28% liquid nitrogen fertilizer and on gallon of molasses were added. The combination was thoroughly mixed and was applied to a plot infested with pigweed, velvetleaf, lambsquarters and cockleburr. The application was at the rate of 0.66 pints per acre. This is approximately one-half of the recommended minimum rate for this herbicide. Basagran TM is a post-emergent herbicide using 3-isopropyl-1H-2,1,3-benzothiadiazin-(4)3H-one,2,2-dioxide. This is an herbicide originated by BASF of West Germany. The molasses and the liquid nitrogen were included to serve as a surfactant. The application was made using a tractor-mounted sprayer with a fan tip nozzle. The boom height was 30 inches above the canopy. The composition was applied at 6:00 p.m. at a temperature of 80° F. The humidity was in the mid-70's and there were overcast skies. The tractor moved at a speed of 5.5 mph during the application. This application did not include the use of sound.

A second strip of the same weed infested field was treated 23 hours later, all conditions being the same except that a sound unit was used throughout the application of the herbicide composition at a frequency of 4 to 6 kilohertz and a volume of 115 decibels. The sound unit was activated five minutes prior to entering the field. The chemical Basagran TM herbicide was applied in an identical manner as on the first piece of land discussed above. The tractor was driven back through this strip of land with the sound unit on but without additional spraying of the chemical composition. The following indicates the percent of eradication for each of the four weeds contained in the field:

| | Treated Only With Herbicide | Treated with Herbicide and Sound |
|---|---|---|
| Pigweed | 6.6 | 45.0 |
| Velvetleaf | 1.6 | 81.6 |
| Lambsquarter | 0.0 | 26.6 |
| Cockleburr | 10.0 | 76.6 |

EXAMPLE VIII

Two test areas were selected, approximately one-quarter mile apart and having weed infestation approximately equal. One test area was sprayed while simultaneously applying sound at a frequency of between 4 and 6 kilohertz and a volume of about 115 decibels. The other strip was only sprayed. In both instances, the composition was the same as the previous Example; however, the application rate was at 1.5 pints of Basagran TM per acre. The strip included 90% burndown of rough pigweed when sound was used and only 65% when no sound was used.

EXAMPLE IX

A similar test as the preceding Example was carried out using Poast grass herbicide added to the previously described Basagran TM mixture. The combination was applied with the Basagran TM at a rate of 1.25 pints per acre. The combination was applied to giant foxtail which was present in a navy bean field. The foxtail was about 6–8 inches above the navy bean canopy, and was approximately 20 inches tall overall. One hour later, an adjoining strip was sprayed with the same composition and at the same application rate. The results indicated 85% kill on the sound treated strip and only 50% kill on the adjoining strip which was only sprayed with the chemical composition.

EXAMPLE X

A first area of a soybean field was treated with the composition set forth in Example VII. The application rate was 1 pint per acre. No sound application was made. The strip was one-quarter mile in length and fourteen rows in width. Two hours later an adjoining fourteen rows of soybeans were treated at the rate of 0.5 pints per acre. This was carried out by increasing the rate of travel of the tractor to provide the desired application rate of chemical. In this instance, sound was applied at a frequency of between 4 and 6 kilohertz and a volume of approximately 115 decibels. No discernable difference was noted between the two strips of beans. In both instances, about 70% eradication of velvetleaf was obtained; 80% kill of cockleburr, thus showing that one can significantly reduce the herbicide usage, providing one uses the sound application of the present invention.

While various specific embodiments and suggested herbicides have been set forth in this application, it is to be recognized that any herbicide that is taken up by the plant in controlling infestation may be used in the present invention, providing the sound application of the present invention is likewise used.

What is claimed is:

1. A process of inhibiting growth of plants that are at least marginally affected by bentazon, comprising:
- applying a growth inhibiting, at least marginally effective, amount of bentazon to said plants; and
- applying to said plants high frequency sound waves for a period of at least 15 seconds at a volume sufficient to facilitate reception of bentazon into said plants.

2. The process of claim 1 wherein sound is applied at a frequency of between 4 and 6 kilohertz and for a time period of at least 30 seconds.

3. The process of claim 2 wherein bentazon is an aqueous solution.

4. The process of claim 3 wherein said plants are broadleaf plants and wherein bentazon is effective for the growth eradication of broadleaf plants.

5. The process of claim 3 wherein said plants are woody plants and wherein bentazon is effective for the growth eradication of woody plants.

6. The process of claim 3 wherein said plants are grass and wherein bentazon is effective for the growth eradication of grasses.

7. A process of growth eradication of plants that are at least marginally affected by bentazon, comprising:
- applying as growth eradicating, at least marginally effective, amount of bentazon to said plants; and
- applying to said plants sound waves at a frequency between 4 and 6 kilohertz, for at least 15 seconds, and at a volume sufficient to open the stoma.

8. The process of claim 7 wherein said plants are a member selected from the group consisting of Canadian thistle, quackgrass, yellow nutsedge, bluegrass, sowthistle, field bindweed, leafy spurge, common milkweed, wirestem muhly, perennial buttercups, germander, bull thistle, cockleburr, chickweed, goldenrod, pigweed, mustards, burdoch, buttonweed, wild sunflowers, ash, wild blackberry, hawthorne, oak, ivy, sumac, maple, willow, chokeberry, poison ivy, mesquite, brambles, wild grape, honeysuckle, alder, pine, fir, spruce, rag weed, pokeberry, yucca, smartweed, clovers, knotweed, shepherds purse, crabgrass, foxtail, coffeeweed, teaweed, kochia, velvetleaf, cockles, knapweed, dock, gooseweed, toadflax, johnsongrass, dandelions, sandbur, groundcherry, morningglory, beggarweed, annual bluegrass, fiddleneck, tarweed, speedwell, and shattercane.

9. A process for treating plants, that are at least marginally affected by bentazon, comprising:
 applying bentazon to the plants in an amount sufficient to inhibit growth; and
 applying sound waves for at least 15 seconds, at a frequency of 4-6 kilohertz, and at a volume of at least 115 decibels.

* * * * *

UNITED STATES PATENT AND TRADEMARK OFFICE
CERTIFICATE OF CORRECTION

PATENT NO. : 5,043,009

DATED : August 27, 1991

INVENTOR(S) : Danis R. Carlson

It is certified that error appears in the above-identified patent and that said Letters Patent is hereby corrected as shown below:

Col. 6, line 54, delete "as", insert --a--.

Signed and Sealed this

Third Day of November, 1992

Attest:

DOUGLAS B. COMER

Attesting Officer

Acting Commissioner of Patents and Trademarks